US006723896B1

(12) United States Patent
Moller et al.

(10) Patent No.: US 6,723,896 B1
(45) Date of Patent: Apr. 20, 2004

(54) INDUCIBLE SITE-SPECIFIC RECOMBINATION FOR THE ACTIVATION AND REMOVAL OF TRANSGENES IN TRANSGENIC PLANTS

(75) Inventors: Simon Geir Moller, New York, NY (US); Jianru Zuo, New York, NY (US); Nam-Hai Chua, Scarsdale, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 09/439,534

(22) Filed: Nov. 12, 1999

(51) Int. Cl.[7] .................. C12N 15/82; C12N 15/87; C12N 15/90; A01H 5/00
(52) U.S. Cl. ............... 800/288; 435/320.1; 435/468; 800/278
(58) Field of Search ................ 435/69.1, 320.1, 435/468, 410, 419, 69.7; 800/278, 288, 295, 298

(56) References Cited

U.S. PATENT DOCUMENTS 5,965,791 A * 10/1999 Ebinuma et al. ............ 800/205
6,063,985 A *  5/2000 Chua et al. .................. 800/278
6,326,192 B1 * 12/2001 Sugita et al. ............ 435/320.1

FOREIGN PATENT DOCUMENTS

EP      0 911 412     4/1999     ........... C12N/15/84
WO     WO 97 37012   10/1997    ........... C12N/15/11

OTHER PUBLICATIONS

Zuo et al., Nature Biotech., 2001, vol. 19, pp. 175–161.*
Sektas, Marian et al., "Tightly controlled two–stage expression vectors employing the Flp/FRT–mediated inversion of cloned genes." *Molecular Biotechnology*, 9:1, pp. 17–24, 1998.
Albert, H. et al. "Site–specific integration of DNA into wild–type and mutant lox sites placed in the plant genome", *The Plant Journal*, 1995; 7(4):649–659.
Aoyama, T. et al. "A glucocorticoid–mediated transcriptional induction system in transgenic plants", *The Plant Journal*, 1997; 11(3):605–612.
Aoyama, T. "Glucocorticoid–inducible Gene Expression in Plants", *Inducible Gene Expression in Plants* (Ed. P. Reynolds), CAB International (Wallingford) (1999), pp. 43–59.
Baron, U. et al. "Generation of conditional mutants in higher eukaryotes by switching between the expression of two genes", *Proc. Natl. Acad. Sci. USA*, Feb. 1999; 96:1013–1018.
Böhner, S. et al. "Transcriptional activator TGV mediates dexamethasone–inducible and tetracycline–inactivatable gene expression", *The Plant Journal*, 1999; 19(1):87–95.
Busch, M.A. et al. "Activation of a Floral Homeotic Gene in Arabidopsis", *Science*, Jul. 23, 1999; 285:585–587.

Caddick, M.X. et al. "An ethanol inducible gene switch for plants used to manipulate carbon metabolism", *Nature Biotechnology*, Feb. 1998; 16:177–180.
Dale, E.C. et al. "Intra– and intermolecular site–specific recombination in plant cells mediated by bacteriophage P1 recombinase", *Gene*, 1990; 91:79–85.
Faiss, M. et al. "Conditional transgenic expression of the ipt gene indicates a function for cytokinins in paracrine signaling in whole tobacco plants", *The Plant Journal*, 1997; 12(2):401–415.
Gatz, C. et al. "Stringent repression and homogeneous de–repression by tetracycline of a modified CaMV 35S promoter in intact transgenic tobacco plants", *The Plant Journal*, 1992; 2(3):397–404.
Gatz, C. "Chemical Control of Gene Expression", *Annu. Rev. Plant Physiol. Plant Mol. Biol.*, 1997; 48:89–108.
Gatz, C. et al. "Promoters that respond to chemical inducers", *Trends Plant Sci.*, Sep. 1998; 3(9):352–358.
Gatz, C. et al. "Tn10–encoded tet repressor can regulate an operator–containing plant promoter", *Proc. Natl. Acad. Sci. USA*, Mar. 1988; 85:1394–1397.
Gossen, M. et al. "Transcriptional Activation by Tetracyclines in Mammalian Cells", *Science*, Jun. 23, 1995; 268:1766–1769.
Kang, H–G et al. "A glucocorticoid–inducible transcription system causes severe growth defects in Arabidopsis and induces defense–related genes", *The Plant Journal*, 1999; 20(1):127–133.
Klee, H.J. et al. "E2. Transgenic Plants in Hormone Biology", in *Plant Hormones* (ed. P.J. Davies) (Kluwer Academic Publishers (Netherlands)) (1995), pp. 340–353.
Kunkel, T. et al. "Inducible isopentenyl transferase as a high–efficiency marker for plant transformation", *Nature Biotechnology*, Sep. 1999; 17:916–919.
Lloyd, A.M. et al. "Epidermal Cell Fate Determination in Arabidopsis: Patterns Defined by a Steroid–Inducible Regulator", *Science*, Oct. 21, 1994; 266:436–439.

(List continued on next page.)

*Primary Examiner*—Ashwin Mehta
(74) *Attorney, Agent, or Firm*—Rothwell, Figg, Ernst & Manbeck, P.C.

(57) ABSTRACT

Disclosed is an inducible promoter system in conjunction with a site-specific recombination system which allows (i) specific activation of transgenes at specific times or (ii) excision and removal of transgenes (e.g., antibiotic resistance markers) from transgenic plants. These "suicide" gene cassettes, including the recombination system itself, can be evicted from the plant genome once their function has been exerted. The system is based on the ability to temporally and spatially induce the expression of CRE recombinase which then binds to directly repeated lox sites flanking the transgene in question leading to the precise excision of the gene cassette. Also disclosed is a method to activate an inverted, and therefore silent, transgene by placing two lox sites in opposite orientations flanking the transgene. This results in inversion of the intervening DNA fragment in the presence of CRE recombinase. This activation can be timed by placing the CRE recombinase under the control of an inducible promoter.

10 Claims, 4 Drawing Sheets

OTHER PUBLICATIONS

Ludwig, S.R. et al. "Lc, a member of the maize R gene family responsible for tissue–specific anthocyanin production, encodes a protein similar to transcriptional activators and contains the myc–homology region", *Proc. Natl. Acad. Sci. USA*, Sep. 1989;86:7092–7096.

Lyznik, L.A. et al. "Heat–inducible expression of FLP gene in maize cells", *The Plant Journal*, 1995; 8(2):177–186.

Maeser, S. et al. "The Gin recombinase of phage Mu can catalyse site–specific recombination in plant protoplasts", *Mol. Gen. Genet.*, 1991; 230:170–176.

Martinez, A. et al. "Ecdysone agonist inducible transcriptional in transgenic tobacco plants", *The Plant Journal*, 1999; 19(1):97–106.

McKenzie, M.J. et al. "Controlled Cytokinin Production in Transgenic Tobacco Using a Copper–Inducible Promoter", *Plant Physiol.*, 1998; 116:969–977.

McNellis, T.W. et al. "Glucocorticoid–inducible expression of a bacterial avirulence gene in transgenic Arabidopsis induces hypersensitive cell death", *The Plant Journal*, 1998; 14(2):247–257.

Medford, J.I. et al. "Alterations of Endogenous Cytokinins in Transgenic Plants Using a Chimeric Isopentenyl Transferase Gene", *The Plant Cell*, Apr. 1989; 1:403–413.

Morris, R.O. "E. Molecular Aspects of Hormone Synthesis and Action. E1. Genes Specifying Auxin and Cytokinin Biosynthesis in Prokaryotes", in *Plant Hormones* (ed. P.J. Davies) (1995) (Kluwer Academic Publishers (Netherlands)), pp. 318–339.

Odell, J.T. et al. "Seed–Specific Gene Activation Mediated by the Cre/lox Site–Specific Recombination System", *Plant Physiol.*, 1994; 106:447–458.

O'Gorman, S. et al. "Recombinase–Mediated Gene Activation and Site–Specific Integration in Mammalian Cells", *Science*, Mar. 1991; 251:1351–1355.

Onouchi, H. et al. "Operation of an efficient site–specific recombination system of Zygosaccharomyces rouxii in tobacco cells", *Nucleic Acids Research*, 1991; 19(23):6373–6378.

Ow, D.W. et al. "Genome Manipulation Through Site–Specific Recombination", *Critical Reviews in Plant Sciences*, 1995; 14(3):239–261.

Redig, P. et al. "Analysis of Cytokinin Metabolism in ipt Transgenic Tobacco by Liquid Chromatography–Tandem Mass Spectrometry", *Plant Physiol.*, 1996; 112:141–148.

Schnell, D.J. "Shedding Light on the Chloroplast Protein Import Machinery", *Cell*, Nov. 17, 1995; 83:521–524.

Svab, Z. et al. "High–frequency plastid transformation in tobacco by selection for a chimeric aadA gene", *Proc. Natl. Acad. Sci. USA*, Feb. 1993; 90:913–917.

Weigel, D. et al. "A developmental switch sufficient for flower initiation in diverse plants", *Nature*, Oct. 12, 1995; 377:495–500.

Weinmann, P. et al. "A chimeric transactivator allows tetracycline–responsive gene expression in whole plants", *The Plant Journal*, 1994; 5(4):559–569.

Sugita, K. et al. "Effective selection system for generating marker–free transgenic plants independent of sexual crossing"; *Plant Cell Reports* (1999); 18:941–947.

* cited by examiner

INDUCIBLE SITE-SPECIFIC RECOMBINATION FOR THE ACTIVATION AND REMOVAL OF TRANSGENES IN TRANSGENIC PLANTS

BACKGROUND OF THE INVENTION

Transgenic techniques have become a powerful tool to address important biological problems in multicellular organisms, and this is particularly true in the plant field. Many approaches that were impossible to implement by traditional genetics can now be realized by transgenic techniques, including the introduction of homologous or heterologous genes into plants, with modified functions and altered expression patterns. The success of such techniques often depends upon the use of markers to identify the transgenic plants and promoters to control the expression of the transgenes.

Selectable markers are widely used in plant transformation. Historically such markers have often been dominant genes encoding either antibiotic or herbicide resistance (Yoder and Goldsbrough, 1994). Although such markers are highly useful, they do have some drawbacks. The antibiotics and herbicides used to select for the transformed cells generally have negative effects on proliferation and differentiation and may retard differentiation of adventitious shoots during the transformation process (Ebinuma et al., 1997). Also, some plant species are insensitive to or tolerant of these selective agents, and therefore, it is difficult to separate the transformed and untransformed cells or tissues (Ebinuma et al., 1997). Further, these genes are constitutively expressed, and there are environmental and health concerns over inserting such constitutively expressed genes into plants which are grown outside of a laboratory setting (Bryant and Leather, 1992; Gressel, 1992; Flavell et al., 1992).

A system to silence or remove such marker genes or other genes or to express them at only desired times would be very useful. Placing such genes under the control of an inducible or tissue-specific promoter has been accomplished. For example, transgenic plants expressing the ipt gene under the control of heat shock- (Medford et al., 1989), light- (Redig et al., 1996), copper- (McKenzie et al., 1998), tetracycline- (Redig et al., 1996; Faiss et al., 1997; Gatz et al., 1992) or dexamethasone- (Kunkel et al., 1999) inducible promoters have been used to study the biological effects of cytokinins. Other inducible systems include the heat-inducible expression system (Lyznik et al., 1995), the ethanol inducible system (Caddick et al., 1998), the ecdysone system (Martinez et al., 1999), and the TGV dexamethasone/tetracycline system (Bohner et al., 1999).

Excision of a marker gene by using the transposable element Ac has been performed, although this occurs at a very low frequency and after a long period of cultivation (Ebinuma et al., 1997). Another method for excising a gene is to use the Cre/lox system. The bacteriophage P1 Cre/lox site-specific recombination system (Dale and Ow, 1990; Odell et al., 1994) consists of two components: (i) a recombinase (CRE) and (ii) recombination sites (lox) at which the recombinase acts. The CRE gene encodes a 38 kDa recombinase which is able, without any other additional factors, to catalyze the recombination between two lox sites. A lox site consists of two inverted 13 bp repeats separated by an asymmetric 8 bp spacer where each inverted repeat acts as a binding site for CRE. The asymmetric nature of the 8 bp spacer gives a directionality to the lox site and determines the type of recombination event. The presence of two inverted lox sites leads to an inversion of the intervening DNA sequence whereas the presence of two directly repeated lox sites results in the excision of the intervening DNA sequence.

There are several site-specific recombination systems that have been shown to work in plants in addition to the described bacteriophage P1 Cre/lox system and these include: (i) the FLP-FRT system from *Saccharomyces cerevisiae* (O'Gorman et al., 1991), (ii) the GIN/gix system from bacteriophage Mu (Maeser and Kahmann, 1991) and (iii) the R/RS system from *Zygosaccharomyces rouxii* (Onouchi et al., 1991).

The FLP-FRT recombination system from *Saccharomyces cerevisiae* is based on site specific recombination by FLP recombinase on FLP recombination target sites (FRT). FRT consists of two inverted 13 base pair repeats and an 8 base pair spacer on which FLP recombinase acts. By inserting two directionally repeated FRT sites flanking a target gene it is possible, by addition of FLP recombinase, to excise the intervening DNA fragment by site-specific eviction. FLP recombinase mediated excision has also been shown to be reversible providing means for the introduction of DNA into specific sites in mammalian chromosomes (O'Gorman et al., 1991).

The Gin invertase encoded by bacteriophage Mu catalyzes the site-specific inversion of the G segment in the bacteriophage. The recombination sites (gix) are 34 base pairs in length and the two sites consist of two inversely oriented half-sites separated by two crossover regions. GIN acts on the gix sites by binding to the two half-sites and mediates DNA exchange and hence DNA inversion.

The R gene from pSR1 from *Zygosaccharomyces rouxii* encodes a recombinase that mediates site-specific recombination between two recombination sites (RS). The RS sites on pSR1 comprise a pair of inverted repeat sequences of 959 base pairs which contain the recombination sites (58 base pairs). Depending on the directionality of the RS sites, the R recombinase can catalyze, without any other additional factors, the excision (directionally repeated) or inversion (opposite orientation) of large DNA fragments (~200 kilobase pairs).

The publications and other materials used herein to illuminate the background of the invention or provide additional details respecting the practice, are incorporated by reference, and for convenience are respectively grouped in the appended List of References.

SUMMARY OF THE INVENTION

The invention is directed to the use of an inducible promoter system in conjunction with a site-specific recombination system in order to (i) specifically activate transgenes at specific times and (ii) to excise and remove transgenes (e.g., antibiotic resistance markers) from trarsgenic plants once used and no longer needed. These "suicide" gene cassettes, including the recombination system itself, can therefore be evicted from the plant genome once their function has been exerted.

The system is based on the ability to temporally and spatially induce the expression of CRE recombinase which then binds to directly repeated lox sites flanking the transgene in question leading to the precise excision of the gene cassette. In order to test this system a construct was designed that allows in planta monitoring of precise excision events using the firefly luciferase (LUC) reporter gene as a marker for recombination.

DETAILED DESCRIPTION OF THE INVENTION

Figure 1:
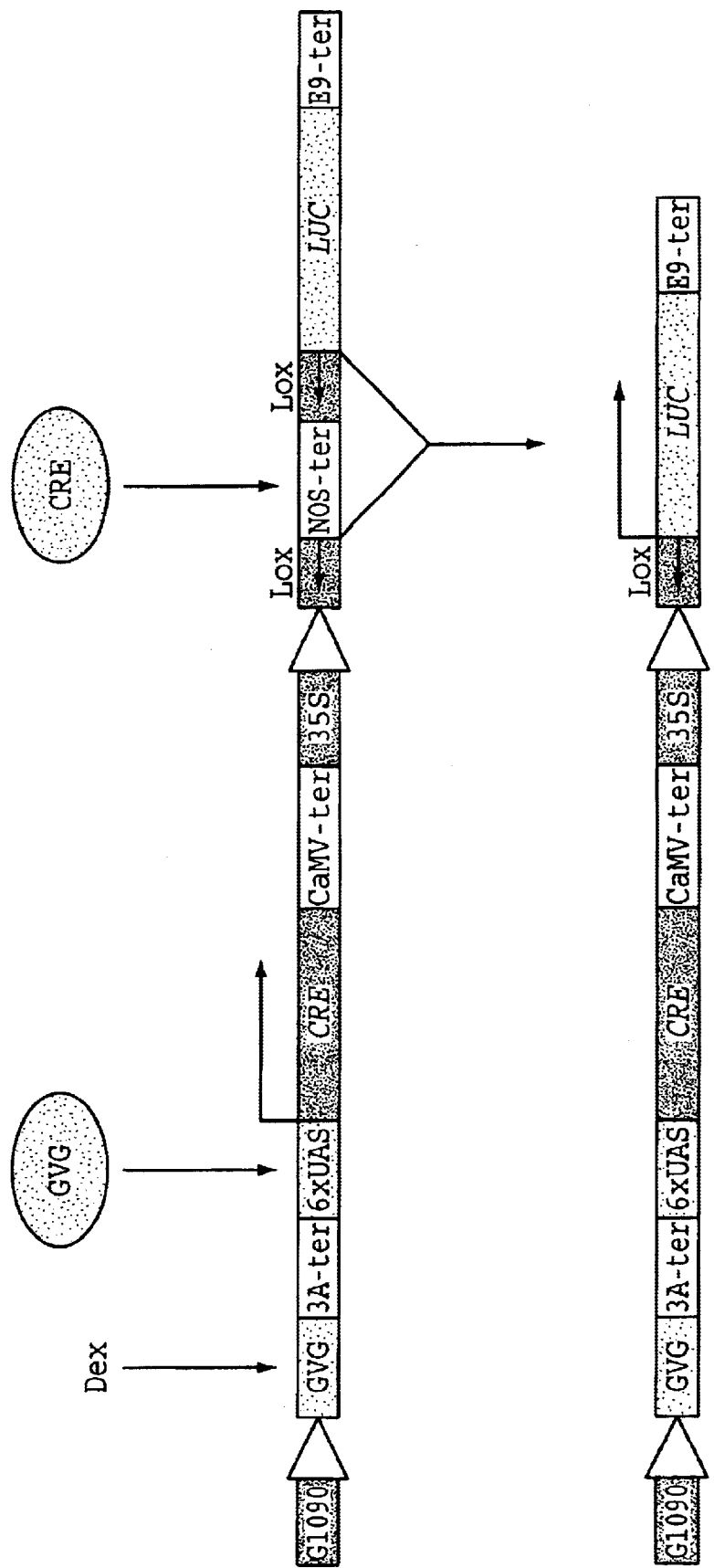
FIG. 1 is a schematic diagram showing pGVG-Cre/lox-luc and the principle of inducible site-specific recombination and eviction of the intervening stuffer-fragment. G1090: promoter (Ishige et al, 1999) driving the tri-hybrid transcription factor GVG; 3A-ter: rbcs 3A polyA addition sequence; 6xUAS: 6x binding site for GVG; CaMV-ter: CaMV polyA addition sequence; NOS-ter: nopaline synthase polyA addition sequence; E9-ter: rbcs E9 polyA addition sequence.

We here demonstrate site-specific excision of DNA fragments from transgenic Arabidopsis plants using the bacteriophage P1 Cre/lox site-specific recombination system in conjunction with the GVG inducible system (U.S. patent application Ser. No. 09/014,592 which is incorporated herein by reference; Aoyama and Chua, 1997). The generated construct, pGVG-Cre/lox-luc, consists of the GVG inducible promoter system (Aoyama and Chua, 1997) driving the expression of CRE and a CaMV 35S promoter driving LUC expression which is transcriptionally blocked by an intervening DNA cassette, a "stuffer-fragment" containing two directly repeated lox sites flanking a NOS polyA additional sequence (FIG. 1).

The system works as follows: (i) Addition of the chemical inducer, the steroid hormone dexamethasone (DEX) in the examples of this disclosure, to transgenic plants leads to a conformational change and "activation" of the trihybrid transcription factor GVG which in turn is able to bind to the 6xUAS promoter sequence and initiate transcription of CRE. (ii) The generated CRE recombinase binds to the directly repeated lox sites giving rise to site-specific recombination and the excision of the NOS terminator. (iii) Following recombination and removal of the NOS terminator the CaMV 35S promoter is able to drive LUC expression which marks the recombination sectors.

We have transformed pGVG-Cre/lox-luc into *Arabidopsis thaliana* and analyzed site-specific recombination events before and after DEX treatment. Transgenic Arabidopsis plants harboring the GVG-Cre/lox-luc transgene were grown under greenhouse conditions for 2 weeks followed by application of DEX. A solution of 20 $\mu$M DEX was applied (painted) onto one marked leaf from various transgenic seedlings. The seedlings were then transferred back to the greenhouse for between 6–12 hours. The marked DEX treated leaf was then excised from the seedlings together with an adjacent non-DEX-treated leaf, placed on a petri dish, followed by application of the firefly luciferase substrate luciferin. All leaves were then monitored for LUC activity using a cooled CCD camera.

Although our system is demonstrated successfully using the GVG inducible system, any inducible or de-repressible expression system will work as efficiently as the example described. Other inducible systems include, but are not limited to, the heat-inducible expression system (Lyznik et al., 1995), the ethanol inducible system (Caddick et al., 1998), the ecdysone system (Martinez et al., 1999), and the TGV dexamethasone/tetracycline system (Bohner et al., 1999).

There are several site-specific recombination systems that have been shown to work in plants in addition to the described bacteriophage P 1 Cre/lox system and these include (i) the FLP-FRT system from *Saccharomyces cerevisiae* (O'Gorman et al., 1991), (ii) the GIN/gix system from bacteriophage Mu (Maeser and Kahmann, 1991) and (iii) the R/RS system from *Zygosaccharomyces rouxii* (Onouchi et al., 1991). Although we have demonstrated eviction using the Cre/lox system, all the above recombination systems can also be used for inducible or de-repressible transgene eviction or activation using any inducible promoter to drive the expression of the described recombinases.

The described example of site-specific recombination involves eviction of a stuffer-fragment to allow activation of a silent transgene. It is also possible to activate genes by site-specific reversion of the intervening DNA fragment when the lox sites are placed in the opposite orientation.

The use of an inducible or de-repressible system in conjunction with a recombination system allows the specific eviction of any single transgene placed between the chosen recombination sites. It is also possible to use a "two-component" system where two inducible systems are employed. This allows inducible activation of the transgene in question (e.g., an antibiotic resistance marker) using one inducer followed by eviction of the entire transgene, including the recombination system, using a second inducer, once the transgene (e.g., an antibiotic resistance marker) has fulfilled its function. Alternatively, inducible promoters with different inducer affinities may be used selectively to activate one transgene and not the other depending on the concentration of the inducer in question. Eviction of transgenes (e.g., antibiotic resistance markers) from the plant genome using Cre-catalyzed excision biology has been reported (Dale and Ow, 1991; Odell et al., 1994). However, these events rely on gene transfer with subsequent excision of the transgene leaving the recombination transgene, linked to a second marker gene, still present in the plant genome.

Although the system described was tested in *Arabidopsis thaliana*, any transformable plant species can be used for this purpose.

The ability to specifically remove transgenes from transgenic plants offers a way of engineering desired genetic traits into crop species without the presence of potentially environmentally unfriendly transgenes such as antibiotic resistance markers. The system can also be used to activate silent transgenes by removal of "stuffer" fragments or by inverting the silent transgene into the correct orientation for functional expression. The site-specific recombination system described has the ability to fulfill these objectives and these can be divided into two broad categories: A) timed activation of a silent transgene by excision or inversion and B) eviction of constitutively expressed genes after usage.

The present invention is described by reference to the following Examples, which are offered by way of illustration and are not intended to limit the invention in any manner. Standard techniques well known in the art or the techniques specifically described below were utilized.

EXAMPLE 1

Timed Activation of a Silent Transgene by Excision or Inversion

A) Removal of "Stuffer" Fragment

This example demonstrates clearly that a silent transgene can be temporally activated. The principle is based on the ability of a terminator sequence to abolish functional expression of a transgene from a constitutive promoter when placed between the promoter and the transgene in question (FIG. 1). By placing two directional lox sites flanking the terminator sequence, here NOS-ter, it is possible by inducible recombinase expression to excise the terminator sequence leading to functional transgene expression. The firefly luciferase (LUC) reporter gene is used as a marker for functional recombination and subsequent transgenic activation. The addition of dexamethasone induces expression of CRE which in turn will cut out the terminator region between the two lox sites. In the absence of dexamethasone, the presence of the NOS-ter between the 35S promoter and the luciferase gene prevents the expression of luciferase. After dexamethasone is added, thereby inducing CRE which cuts out NOS-ter, the LUC gene is controlled by the CaMW 35S promoter and is expressed. This gene remains expressed even after withdrawal of dexamethasone. The LUC gene is here used only as an example because its expression is easily observed. It can be replaced by any other desired gene which will similarly be silent prior to addition of dexamethasone, but will be turned on by addition of dexamethasone and will remain on after withdrawal of dexamethasone.

Figure 2A:
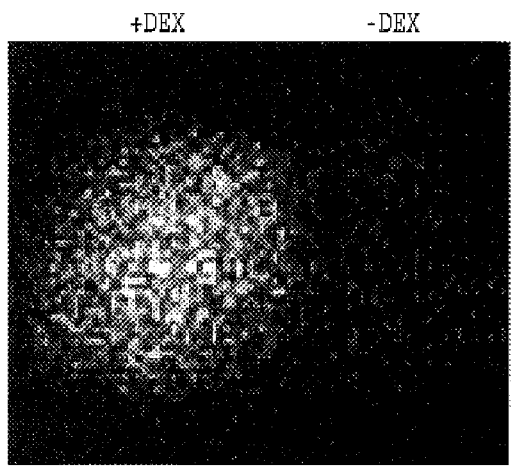
FIGS. 2A–B show DEX treated and non-DEX treated leaves from two independent transgenic Arabidopsis lines showing inducible site-specific recombination and eviction of the "stuffer-fragment". Positive recombination sectors are shown by luciferase activity.
Figure 2B:
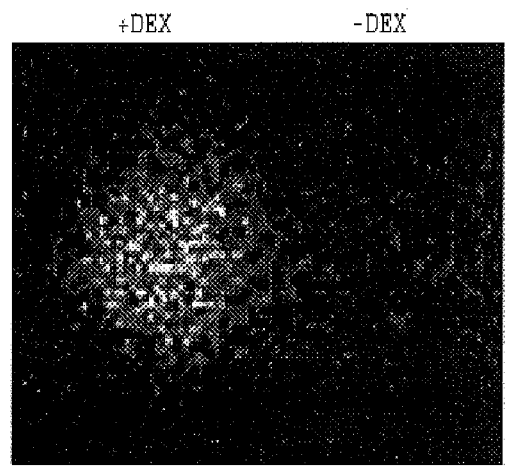

As can be seen from FIGS. 2A–B, the application of DEX induces site-specific recombination in leaves of transgenic Arabidopsis seedlings. It is also clear that the system shows no non-specific induction as is evident from the lack of luciferase activity in non-treated leaves. For applied applications the LUC gene can simply be replaced by any transgene. An example illustrating this is given below.

The expression of floral homeotic genes in Arabidopsis depends on the action of meristem-identity genes such as LEAFY, which encodes a transcription factor that determines whether a meristem will generate flowers instead of leaves and shoots. LEAFY participates in the activation of homeotic genes, which are expressed in specific regions of the flower (Busch et al., 1999) and it has been shown that ectopic expression of LEAFY leads to flower induction in transgenic aspen (Weigel and Nilsson, 1995).

Using the developed site-specific recombination system it is possible to generate timed activation of LEAFY in transgenic trees which show desired traits such as rapid growth in the field after several years. Treated trees will flower and set seed which can be used immediately for propagation by somatic embryogenesis.

B) Inversion of a Transgene.

Figure 3:
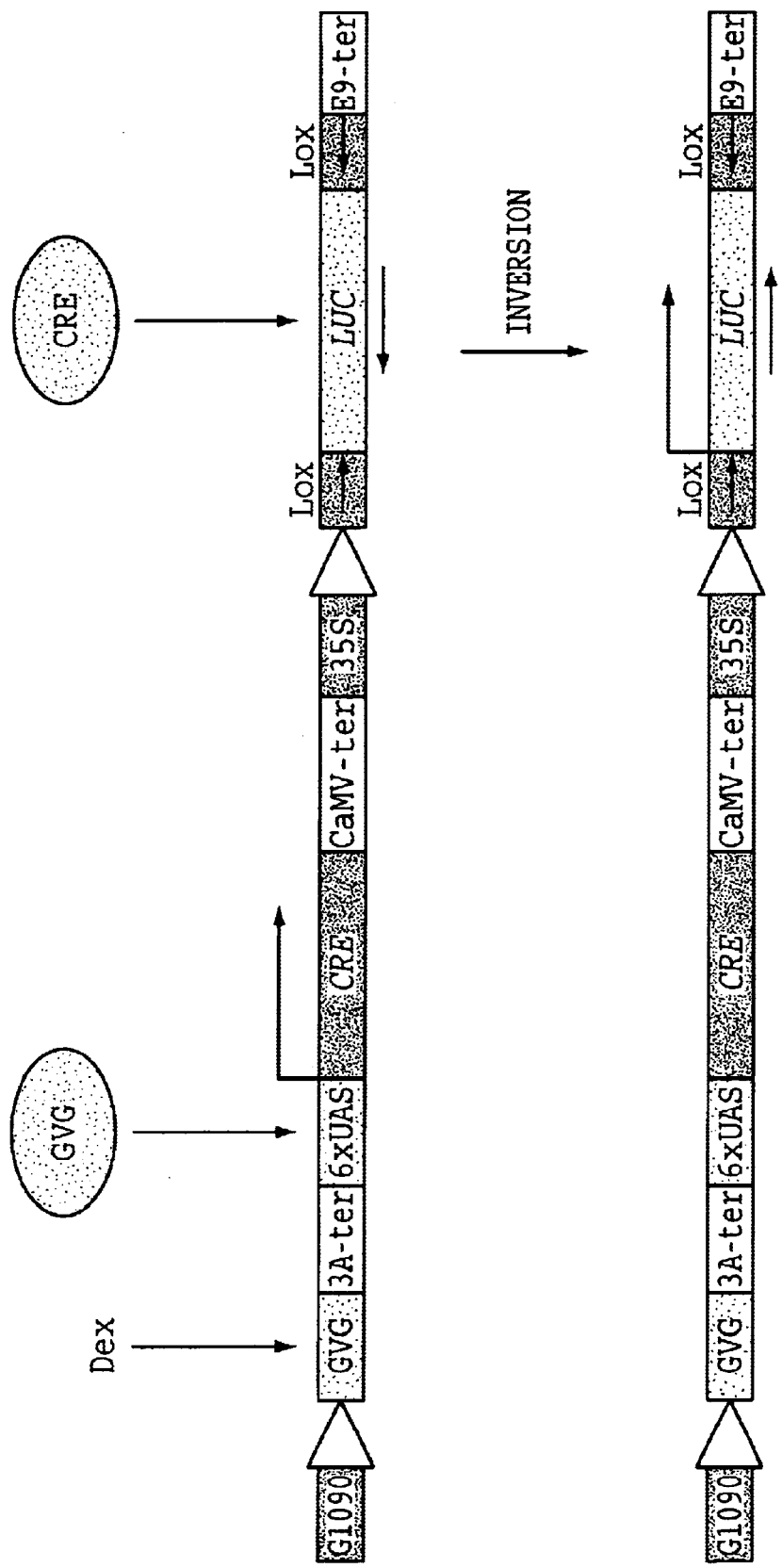
FIG. 3 is a schematic diagram showing the principle of inducible site-specific inversion of an intervening transgene. G1090: promoter driving the tri-hybrid transcription factor GVG; 3A-ter: rbcs 3A polyA addition sequence; 6xUAS: 6x binding site for GVG; CaMV-ter: CAMV polyA addition sequence; NOS-ter: nopaline synthase polyA addition sequence; E9-ter: rbcs E9 polyA addition sequence.

Placing two lox sites in the opposite orientation leads to inversion of the intervening DNA fragment. Using the site-specific recombination system it is possible to activate silent transgenes by timed inversion of the transgene in question (FIG. 3). Placing the transgene in an antisense orientation behind a constitutive promoter leads to non-functional expression of the tnansgene. Timed expression of the recombinase leads to site-specific inversion of the transgene into the sense orientation which in turn leads to transgene activation. This approach, although feasible, has the disadvantage that the recombination event is reversible due to the continual presence of both recombination sites after recombination. This in effect means that the intervening DNA fragment can be "flipped" back and forth during the presence of the recombinase.

EXAMPLE 2

Eviction of Constitutively Expressed Genes After Usage

A) Constitutive Expression of a Marker Transgene Followed by Inducible Excision.

Figure 4:
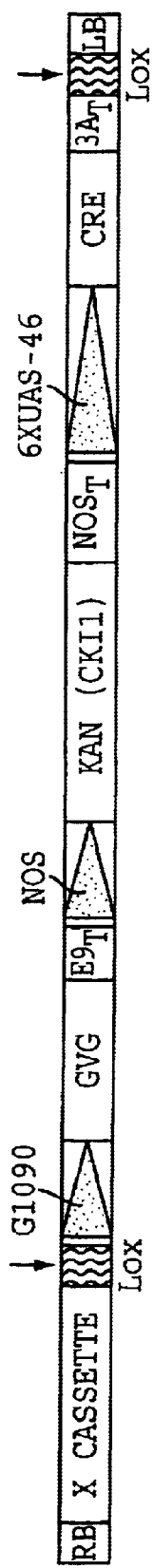
FIG. 4 is a schematic diagram of a binary vector enabling constitutive expression of a marker transgene followed by inducible excision of the DNA cassette. X Cassette: transgene encoding genetic trait of interest; G1090: promoter driving the tri-hybrid transcription factor GVG; $3A_x$: rbcs 3A polyA addition sequence; 6xUAS: 6x binding site for GVG; $NOS_x$: nopaline synthase polyA addition sequence; $E9_x$: rbcs E9 polyA addition sequence; NOS: nopaline synthase promoter.

The transformation of any plant species requires a selectable marker in order to identify individuals that have been successfully transformed with the transgene in question. This is normally performed using either an antibiotic resistance marker gene such as npt II and hpt II or a gene coding for shoot regeneration properties such as isopentenyl transferase (Kunkel et al., 1999) as part of the transgene cassette which in turn becomes integrated into the plant genome together with the desired genetic trait. The described inducible recombination system can be used to remove the "marker" gene once transformed plants have been regenerated and selected for successful transgene integration leaving behind only the transgene (genetic trait) of interest. The underlying principle is as follows: A plant transformation binary vector is constructed containing the following between the left and right border integration sequences (FIG. 4): (i) the gene of interest (X Cassette), (ii) constitutive expression of a marker gene, e.g., kanamycin or CKI1 under the control of a NOS promoter as shown in FIG. 4, and (iii) inducible expression of a recombinase, e.g., use of the GVG system in combination with CRE which is controlled by a 6×UAS promoter as shown in FIG. 4. The order of the internal sequences need not be that shown in FIG. 4. The cassette containing the marker gene and the recombinase is flanked by two directly repeated recombination sites.

Upon transfection with the vector, transfected plants or cells are identified via the marker which is constitutively expressed. After selection of transfected plants or cells, the selected plants or cells are treated with DEX which binds to GVG, this complex in turn binds to the 6×UAS causing induction of CRE which then excises the complete region of the vector between the two lox sites thereby leaving only the RB, X Cassette, one copy of lox, and the LB. This system allows for the regeneration of transgenic plants containing the gene of interest by virtue of marker gene selection followed by marker gene eviction by site-specific recombination in response to an inducer.

B) Inducible Expression of a Marker Transgene Followed by Inducible Excision

Figure 5:
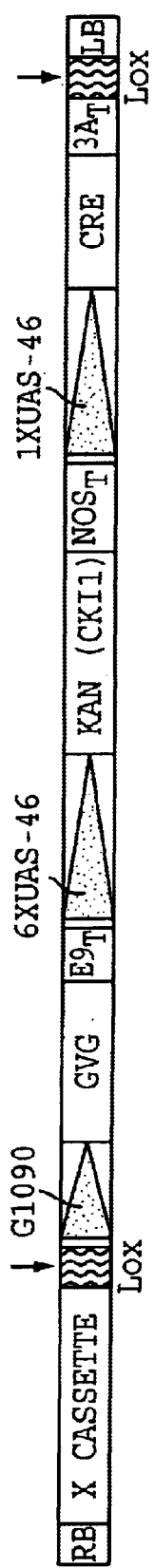
FIG. 5 is a schematic diagram of a binary vector enabling inducible expression of a marker transgene followed by inducible excision of the DNA cassette. X Cassette: transgene encoding genetic trait of interest; G1090: promoter driving the tri-hybrid transcription factor GVG; $3A_x$: rbcs 3A polyA addition sequence; 6xUAS: 6x binding site for GVG (high affinity); 1xUAS: 1x binding site for GVG (low affinity); $NOS_x$: nopaline synthase polyA addition sequence; $E9_T$: rbcs E9 polyA addition sequence; NOS: nopaline synthase promoter.

Inducible promoter systems can be manipulated so that their affinity towards the inducer varies. In this respect it is possible to construct a site-specific recombination system where both the marker gene and the recombinase are under the control of the same inducible promoter but harbor different affinities towards the inducer in question. The underlying principle is as follows: A plant transformation binary vector is constructed containing the following between the left and right border integration sequences (FIG. 5) (i) the gene of interest (X Cassette), (ii) inducible expression of a marker gene (e.g., kanamycin or CKI1) using a high affinity promoter (here, 6×UAS), and (iii) inducible expression of a recombinase (e.g., CRE) using a low affinity promoter (here, 1×UAS). The order of the internal sequences need not be in the order as shown in FIG. 5. The cassette containing the marker gene and the recombinase is flanked by two directly repeated recombination sites (lox is used in this example).

To use this system, plants or cells are transfected with the vector. Addition of an inducer (DEX in this example) at a low level induces the gene under the control of the high affinity (6×UAS) promoter but not the low affinity (1×UAS) promoter. In the example, a low level of DEX induces kanamycin or CKI1 which can be used to select transfected cells or plants. After the transfected cells or plants are selected, they are treated with a high level of inducer which then binds enough GVG to be at a high enough concentration to bind the 1×UAS to induce synthesis of CRE. The CRE then cuts out the vector region between the two lox sites, thereby leaving only the RB, X Cassette, one copy of lox and the LB as the integrated nucleic acid.

This system allows for the regeneration of transgenic plants by induction of the marker gene using low concentrations of the inducer followed by marker gene eviction using high concentrations of the inducer. The use of inducible promoters, only differing in their inducer affinities, to activate both the marker gene and the recombinase has the added advantage of controllable marker gene activation which may be important when using marker genes encoding proteins involved in shoot regeneration or developmental patterns.

A further improvement of this system is the use of mutant recombination sites with lower affinity towards the recombinase. Mutant lox sites showing lower affinity towards CRE have been demonstrated (Albert et al. 1995) and ensure that the eviction of the transgene does not occur prior to increasing the concentration of the inducer, i.e., due to leaky expression of CRE.

EXAMPLE 3

Inducible Eviction or Activation of Chloroplast Encoded Transgenes

Horizontal gene transfer of foreign nuclear encoded genes, especially selectable marker genes such as antibiotic resistance genes, from transgenic plants via pollen is of environmental concern. One way of overcoming this potential problem is to contain the foreign genes in the plastids since plastid encoded genes are not transmitted by pollen. High frequency plastid transformation has been shown for tobacco (Svab and Maliga, 1993) and can be performed for a number of plant species. One way to overcome the potential danger of horizontal gene transfer via pollen is to couple plastid transformation with inducible eviction of the chloroplast localized selectable marker gene cassette after successful selection. The principle of the system is effectively identical to the described Example 2 with the following modifications. The transgene cassette harboring a constitutively selectable marker gene, such as an antibiotic resistance marker, flanked by directly repeated lox sites resides in the plastid genome. After positive selection of transgenic plants CRE is induced as described previously, however in this case the gene for the CRE recombinase has been engineered to contain extra DNA sequences encoding an N-terminal transit peptide for chloroplast targeting (Schnell, 1995). Upon addition of the inducer, CRE recombinase is generated and translocated to the plastids where it acts upon the lox sites and removes the selectable marker gene cassette. The principle of Example 1 can also be applied and this system can also be used for the inducible eviction or activation of any chloroplast encoded transgene by the appropriate placement of the lox sites.

EXAMPLE 1

Localized Activation or Eviction

The site-specific recombination system disclosed above and any variation using the described recombination and inducible or de-repressible promoter systems can be used for the permanent activation of a transgene at tissue specific locations within a plant.

The Arabidopsis ttg mutant lacks both trichomes and anthocyanin pigment (Lloyd et al., 1994). This mutant phenotype can be reversed by the expression of the maize regulatory R (which requires a second regulator C1), which is required in maize for the expression of anthocyanin. The R protein contains acidic and basic HLH domains with strong homology to the HLH domains of mammalian MYC transcriptional regulators. It is possible to use the described inducible site-specific transgene activation system to create transgenic ttg plants that can activate R gene expression and hence anthocyanin production at specific regions which will be constitutively expressed throughout the life cycle of the plant.

Overexpression of the R gene in wild type Arabidopsis and other plants, such as tobacco or tomato, can cause anthocyanin production. We can therefore use the Cre/lox system together with selective application of the inducer, using a template such as a leaf, to make specific patterns that express anthocyanin.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Albert H, Dale E C, Lee E and Ow D W (1995). *Plant J*. 7:649–659.

Aoyamra T and Chua N-H(1997). *Plant J*. 11:605–612.

Bohner S, Lenk I, Rieping M, Herold M and Gatz C (1999). *Plant J*. 19:87–95.

Bryant J and Leather S (1992). *Trends Biotechnol.* 10:274–275.

Busch M A, Bomblies K and Weigel D (1999). *Science* 285:585–587.

Caddick M X, Greenland A J, Jepson 1, Krause K P, Qu N, Riddell K V, Salter M G, Schuch W, Sonewald U and Tomsett A B (1998). *Nat. Biotechnol.* 16:177–180.

Dale E C and Ow D W (1990). *Gene* 91:79–85.

Ebinuma H, Sugita K, Matsunaga E and Yamakado M (1997). *Proc. Natl. Acad Sci. USA* 94:2117–2121.

Faiss M, Zalubilova J, Strnad M and Schmülling T (1997). *Plant J*. 12:401–415.

Flavell R B, Dart E, Fuchs R L and Fraley R B (1992). *Bio/Technology* 10:141–144.
Gatz C, Frohberg C and Wendenburg R (1992). *Plant J.* 2:397–404.
Gressel J (1992). *Trends Biotechnol.* 10:382.
Ishige et al. (1999). *Plant J.* 18:443–448.
Kunkel T, Niu Q-W, Chan Y-S and Chua N-H (1999). *Nature Biotechnology* 17:916–919.
Lloyd A M, Schena M, Walbot V and Davis R W (1994). *Science* 266:436–439.
Lyznik L A, Hirayarna L, Rao K V, Abad A and Hodges T K (1995). *Plant J.* 8:177–186.
Maeser S and Kahmann R (1991). *Mol. Gen. Genet.* 230:170–176.
Martinez A, Sparks C, Hart C A, Thompson J and Jepson I (1999). *Plant J.* 19:97–106.
McKenzie M J, Mett V, Reynolds P H S and Jameson P E (1998). *Plant Physiol.* 116:969–977.
Medford J I, Horgan B R, El-Sawi Z and Klee H J (1989). *Plant Cell* 1:403–413.
Odell J T, Hoopes J L and Vermerris W (1994). *Plant Physiol.* 106:447–458.
O'Gorman S, Fox D T and Wahl G M (1991). *Science* 251:1351–1355.
Onounchi H, Yokoi K, Machida C, Matsuzaki H, Oshima Y, Matsuoka K, Nakamura K and Machida Y (1991). *Nucleic Acids Res.* 19:6373–6378.
Redig P, Schmülling T and Van Onckelen H (1996). *Plant Physiol.* 112:141–148.
Schnell D J (1995). *Cell* 83:521–524.
Svab Z and Maliga P (1993). *Proc. Natl. Acad. Sci. USA* 90:913–917.
Weigel D and Nilsson O (1995). *Nature* 377:495–500.
Yoder J I and Goldsbrough A P (1994). *Bio/Technology* 12:263–267.
U.S. patent application Ser. No. 09/014,592

What is claimed is:

1. A plant transformation vector comprising a gene of interest, a gene encoding a transcription factor, an inducible gene encoding a recombinase under the control of a vertebrate hormone inducible promoter system, and a pair of recombination sites, wherein said recombination sites flank a marker gene.

2. The vector of claim 1 wherein said pair of recombination sites flanks said marker gene and said inducible gene, and said recombinase causes deletion of said marker gene and said inducible gene.

3. The vector of claim 1 wherein said inducible gene encodes CRE, FLP, GIN or R.

4. The vector of claim 1 wherein said recombination sites are lox, FRT, gix or RS.

5. The vector of claim 4 wherein said lox sites are mutant and have a lower affinity for CRE than does wild-type lox.

6. The vector of claim 1 wherein said marker gene is under the control of a high affinity vertebrate hormone inducible promoter, and said inducible gene is under the control of a low affinity vertebrate hormone inducible promoter, wherein said high affinity vertebrate hormone inducible promoter is induced by a vertebrate hormone at a low concentration and said low affinity vertebrate hormone inducible promoter is induced by said vertebrate hormone at a high concentration.

7. A method for excising a marker gene from the genome of a germ line cell of a transgenic plant, comprising:

a) transfecting a plant cell with the vector of claim 1 to effect stable transformation of said plant cell;

b) regenerating a transgenic plant from said stably transformed plant cell; and c) exposing said transgenic plant to an inducer to induce the vertebrate hormone inducible promoter system, wherein said inducer induces said vertebrate hormone inducible promoter system so as to effect expression of said recombinase in a germ line cell of said transgenic plant, followed by excision of said marker gene from the genome of said germ line cell, such that said marker gene is not inherited by the progeny of said transgenic plant.

8. A transformed plant comprising the vector of claim 1.

9. The vector of claim 1, wherein the hormone inducible promoter system is the GVG inducible promoter system.

10. The method of claim 7, wherein the hormone inducible promoter system of the vector is the GVG inducible promoter system.

* * * * *